US010813735B2

(12) United States Patent
Erickson et al.

(10) Patent No.: US 10,813,735 B2
(45) Date of Patent: Oct. 27, 2020

(54) POULTRY INJECTION APPARATUS WITH ROTATING CAPTURE MEMBERS AND METHODS OF USE

(71) Applicant: NOVA-TECH ENGINEERING, LLC, Willmar, MN (US)

(72) Inventors: Matthew Erickson, Spicer, MN (US); Scott C. Johnson, Blomkest, MN (US)

(73) Assignee: Nova-Tech Engineering, LLC, Willmar, MN (US)

( * ) Notice: Subject to any disclaimer, the term of this patent is extended or adjusted under 35 U.S.C. 154(b) by 107 days.

(21) Appl. No.: 16/301,112

(22) PCT Filed: May 15, 2017

(86) PCT No.: PCT/US2017/032646
§ 371 (c)(1),
(2) Date: Nov. 13, 2018

(87) PCT Pub. No.: WO2017/200918
PCT Pub. Date: Nov. 23, 2017

(65) Prior Publication Data
US 2019/0133734 A1 May 9, 2019

Related U.S. Application Data

(60) Provisional application No. 62/337,171, filed on May 16, 2016.

(51) Int. Cl.
*A61D 1/02* (2006.01)
*A61D 7/00* (2006.01)
(Continued)

(52) U.S. Cl.
CPC ............... *A61D 1/025* (2013.01); *A61D 7/00* (2013.01); *A61M 5/20* (2013.01); *A61M 5/326* (2013.01);
(Continued)

(58) Field of Classification Search
CPC . A61D 7/00; A61D 1/025; A61D 3/00; A61D 1/005; A61D 1/02; A61D 1/00
(Continued)

(56) References Cited

U.S. PATENT DOCUMENTS

| 4,681,565 A | 7/1987 | Gourlandt |
| 5,199,952 A | 4/1993 | Marshall, Sr. et al. |

(Continued)

FOREIGN PATENT DOCUMENTS

| CN | 1360483 A | 7/2002 |
| CN | 200939276 Y | 8/2007 |

(Continued)

OTHER PUBLICATIONS

International Patent Application No. PCT/US2017/032646, filed May 15, 2017; International Preliminary Report on Patentability dated May 15, 2018; 18 pages.
(Continued)

*Primary Examiner* — Yvonne R Abbott-Lewis
(74) *Attorney, Agent, or Firm* — Mueting Raasch Group

(57) ABSTRACT

Poultry injection apparatus with rotating capture members and methods of using the same are described herein. Each injection apparatus may include one or more rotating capture members and an injection unit configured to move an injection needle between an injection position and a retracted position relative to the one or more capture members.

20 Claims, 7 Drawing Sheets

(51) Int. Cl.
*A61M 5/20* (2006.01)
*A61M 5/32* (2006.01)
*A61M 5/42* (2006.01)
*A61M 5/46* (2006.01)
*A01K 1/06* (2006.01)

(52) U.S. Cl.
CPC .......... *A61M 5/3287* (2013.01); *A61M 5/425* (2013.01); *A61M 5/46* (2013.01); *A01K 1/0613* (2013.01); *A61M 2005/206* (2013.01)

(58) Field of Classification Search
USPC .......................................... 119/751, 417, 713
See application file for complete search history.

(56) References Cited

U.S. PATENT DOCUMENTS

| | | | |
|---|---|---|---|
| 5,364,362 | A | 11/1994 | Schulz |
| 5,651,731 | A | 7/1997 | Gorans et al. |
| 5,927,234 | A * | 7/1999 | Siegel ...................... A61D 3/00 119/417 |
| 6,293,925 | B1 | 9/2001 | Safabash et al. |
| 6,634,319 | B1 | 10/2003 | Zermoglio et al. |
| 6,923,762 | B1 | 8/2005 | Creaghan, Jr. |
| 7,066,112 | B2 | 6/2006 | Gorans |
| 10,398,854 | B2 | 9/2019 | Fenster et al. |
| 10,412,928 | B1 * | 9/2019 | Qamar ................. A01K 1/0613 |
| 2007/0089557 | A1 | 4/2007 | Solomon et al. |
| 2007/0156121 | A1 | 7/2007 | Millman et al. |
| 2012/0203164 | A1 | 8/2012 | Bitton et al. |
| 2014/0031790 | A1 | 1/2014 | Johnson |
| 2015/0290401 | A1 | 10/2015 | Barnes et al. |

FOREIGN PATENT DOCUMENTS

| | | |
|---|---|---|
| CN | 103402459 A | 11/2013 |
| CN | 104755119 A | 1/2015 |
| EP | 0148692 A3 | 7/1985 |
| EP | 0 916 330 A1 | 5/1999 |
| EP | 2 510 911 A1 | 10/2012 |
| EP | 2 630 980 A1 | 8/2013 |
| FR | 2 057 514 | 5/1971 |
| FR | 2 579 100 A1 | 9/1986 |
| FR | 2930425 A1 | 10/2009 |
| JP | 2015-144637 A | 8/2015 |
| WO | WO 2010/085718 A2 | 7/2010 |
| WO | WO 2011/085719 A2 | 7/2010 |
| WO | WO 2012/100151 A1 | 7/2012 |
| WO | WO 2013/104414 A1 | 7/2013 |
| WO | WO 2015/004428 A1 | 1/2015 |

OTHER PUBLICATIONS

International Patent Application No. PCT/US2017/032646, filed May 15, 2017; International Search Report / Written Opinion dated Sep. 22, 2017; 13 pages.

Chinese Patent Application No. 2017800301227 filed Nov. 15, 2018, First Office Action and Search Report dated Aug. 3, 2020, 10 pages.

* cited by examiner

POULTRY INJECTION APPARATUS WITH ROTATING CAPTURE MEMBERS AND METHODS OF USE

CROSS-REFERENCE TO RELATED APPLICATION

This application is the § 371 U.S. National Stage of International Application No. PCT/US2017/032646, filed 15 May 2017, which claims the benefit under 35 U.S.C. § 119 of U.S. Provisional Application Ser. No. 62/337,171 filed 16 May 2016 titled POULTRY INJECTION APPARATUS WITH ROTATING CAPTURE MEMBERS AND METHODS OF USE, the disclosures of which are incorporated herein by reference in their entireties.

Poultry injection apparatus with rotating capture members and methods of using the same are described herein.

The processing of poultry may include activities such as sexing to determine gender, inoculating or otherwise medicating the birds, feeding the birds, weighing the birds, treating the beaks and/or claws of the birds (to, e.g., retard their growth), etc. Conventionally, birds are handled manually, i.e., individuals must physically hold the bird to perform the injection process.

When injecting poultry to, e.g., deliver a medication or some other therapeutic substance, vitamins, or any other substance that should or could be advantageously delivered subcutaneously, the injection process may be complicated by the smaller size of the birds and their movement.

SUMMARY

Poultry injection apparatus with rotating capture members and methods of using the same are described herein. Each injection apparatus may, in one or more embodiments, include one or more rotating capture members and an injection unit configured to move an injection needle between an injection position and a retracted position relative to the one or more capture members.

One potential advantage of the injection apparatus and methods described herein is that, in some embodiments, rotation of one or more capture members may cause the skin of the bird to fold or bunch up in a repeatable manner at an injection location to enhance subcutaneous delivery of the substances delivered using the injection needles that can be inserted into the skin of the bird.

Although the injection apparatus and methods described herein may be used with birds of any age, they may be particularly useful when used with hatchlings, where "hatchlings" are defined as young birds (e.g., chickens, turkeys, ducks, geese, etc.) with an age of one week or less.

In one aspect, one or more embodiments of an injection apparatus as described herein may include: an engagement system comprising a first capture member and a second capture member positioned to define a capture gap between the first capture member and the second capture member, wherein the first capture member is configured to rotate about a first axis in a capture direction, wherein skin of a bird contacting the first capture member in the capture gap is pushed towards the second capture member by the first capture member rotating in the capture direction. The injection apparatus may further include an injection unit operably coupled to the engagement system, wherein the injection unit comprises an injection needle and a needle actuator operably connected to the injection needle, wherein the needle actuator is configured to move the injection needle between an injection position and a retracted position, wherein the injection needle moves towards the first and second capture members when moving from the retracted position to the injection position.

In one or more embodiments of the injection apparatus as described herein, the injection needle comprises a tip portion, wherein the tip portion is located between the first and second capture member when the injection needle is in the injection position.

In one or more embodiments of the injection apparatus as described herein, the injection needle moves between the injection position and the retracted position along an injection axis, wherein the injection axis is aligned with the first axis.

In one or more embodiments of the injection apparatus as described herein, the first capture member comprises a first roller and teeth extending radially outward from the first roller, wherein the teeth of the first capture member rotate about the first axis when the first capture member rotates about the first axis. In one or more embodiments, the teeth of the first capture member are flexible such that the teeth of the first and second capture members elastically deflect when the first capture member is rotated past a location at which the teeth and the second capture member both contact the skin of the bird in the capture gap. In one or more embodiments, the second capture member comprises a second roller and teeth extending radially outward from the second roller, wherein the teeth of the first capture member mesh with the teeth of the second capture member.

In one or more embodiments of the injection apparatus as described herein, the second capture member is configured to rotate about a second axis, wherein the first axis is aligned with the second axis, wherein the first capture member rotates in a clockwise direction about the first axis when rotating about the first axis in the capture direction and the second capture member rotates in a counterclockwise direction about the second axis to draw the skin of a the bird into the capture gap or the first capture member rotates in a counterclockwise direction about the first axis when rotating about the first axis in the capture direction and the second capture member rotates in a clockwise direction about the second axis to draw the skin of a the bird into the capture gap. In one or more embodiments, the first axis is parallel to the second axis.

In one or more embodiments of the injection apparatus as described herein, the injection apparatus further includes a sanitizing apparatus configured to sanitize the injection needle. In one or more embodiments, the sanitizing apparatus is configured to spray sanitizing liquid at the injection needle when the injection needle is in the retracted position.

In one or more embodiments of the injection apparatus as described herein, the injection apparatus comprises a controller operably connected to the first capture member, wherein the controller is configured to rotate the first capture member in the capture direction about the first axis for a selected period of time after the bird is at least partially located in the capture gap.

In one or more embodiments of the injection apparatus as described herein, the injection apparatus comprises a controller operably connected to the first capture member, wherein the controller is configured to rotate the first capture member in the capture direction about the first axis until a rotational force is exerted on one or both of the capture members by the skin of a bird positioned in the capture gap.

In one or more embodiments of the injection apparatus as described herein, the injection apparatus comprises a controller operably connected to the first capture member, wherein the controller is configured to rotate the first capture member in the capture direction about the first axis over a selected angular range after the bird is at least partially located in the capture gap.

In one or more embodiments of the injection apparatus as described herein, the injection needle moves five millimeters or more between the injection position and the retracted position.

In one or more embodiments of the injection apparatus as described herein, the injection unit further comprises a needle position sensor configured to determine a location of the injection needle in the injection position.

In another aspect, one or more embodiments of the methods described herein may include: positioning skin of a bird in a capture gap between a first capture member and a second capture member; rotating the first capture member in a capture direction about a first axis to push the skin of the bird in the capture gap towards the second capture member; advancing an injection needle into an injection position after rotating the first capture member in the capture direction; delivering selected material into the bird through the injection needle after advancing the injection needle into the injection position; and retracting the injection needle to a retracted position from the injection position after delivering the selected material.

In one or more embodiments of the methods described herein, the first capture member rotates about the first axis in a release direction after retracting the injection needle to the retracted position, wherein the release direction rotation is opposite the capture direction rotation.

In one or more embodiments of the methods described herein, the method further comprises rotating the second capture member in a second capture direction about a second axis when rotating the first capture member about the first axis, wherein the second capture member pushes the skin of the bird towards the first capture member when the second capture member rotates in the second capture direction. In one or more embodiments, the second capture member rotates about the second axis in a release direction after retracting the injection needle to the retracted position, wherein the release direction rotation is opposite the capture direction rotation.

In one or more embodiments of the methods described herein, the method further comprises positioning the first and second capture member away from the skin of the live bird after releasing the skin of the live bird.

In one or more embodiments of the methods described herein, the method further comprises sanitizing the injection needle, after retracting the injection needle to the retracted position.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

Where used herein, the terms "top" and "bottom" are used for reference relative to each other only and, depending on the orientation of the apparatus when used, may or may not accurately describe the relative positions of the recited features with respect to the ground.

The above summary is not intended to describe each embodiment or every implementation of the poultry injection apparatus with rotating capture members and methods of using the same as described herein. Rather, a more complete understanding of the invention will become apparent and appreciated by reference to the following Description of Illustrative Embodiments and claims in view of the accompanying figures of the drawing.

BRIEF DESCRIPTION OF THE VIEWS OF THE DRAWING

Illustrative embodiments of the invention will be further described with reference to the views of the drawing, wherein.

DESCRIPTION OF ILLUSTRATIVE EMBODIMENTS

Figure 1:
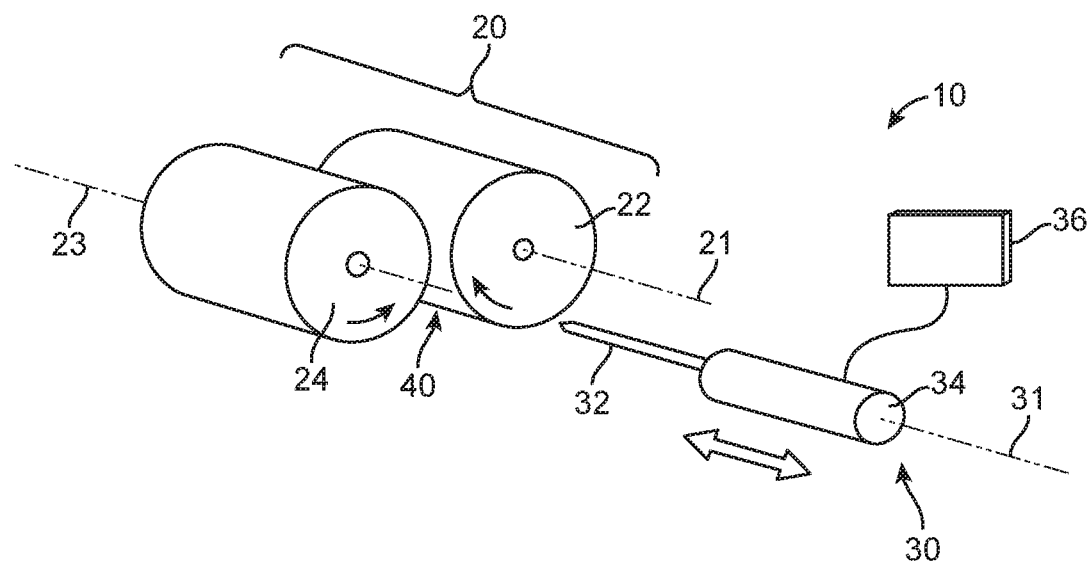
FIG. 1 is a perspective schematic diagram of one illustrative embodiment of an injection apparatus as described herein with an injection needle in a retracted position.
Figure 2:
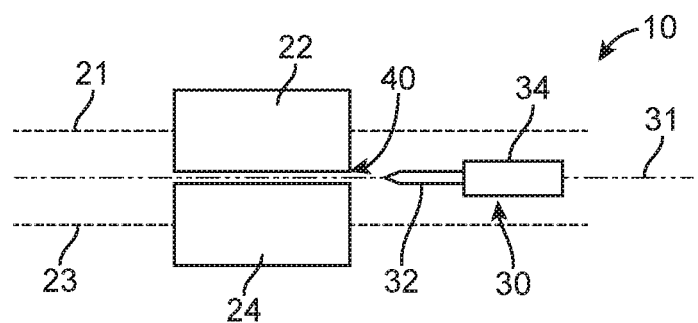
FIG. 2 is a top view of the injection apparatus of FIG. 1.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Illustrative embodiments of injection apparatus and methods of using the same as described herein may be used to subcutaneously inject materials into birds that are carried in poultry carriers similar to those described in International Publication No. WO 2010/085718 titled POULTRY CARRIERS AND METHODS OF RESTRAINING POULTRY. It should, however, be understood that the injection apparatus and methods described herein may be used in the absence of those carriers, e.g., the birds to be processed using the injection apparatus and methods described herein may be held in any suitable jig, fixture, etc. that positions the bird properly for processing.

Further, the injection apparatus and methods described herein may be used in processing systems and methods such as those described in U.S. Pat. No. 7,066,112, titled AUTOMATED POULTRY PROCESSING METHOD AND SYSTEM. The injection apparatus and methods described herein may also be used in other systems or environments where transport and/or processing of birds is performed.

In one or more embodiments of the injection apparatus as described herein an engagement system may be used to create folded or bunched skin on a bird such that an injection needle can be inserted into the folded or bunched skin to facilitate injection of one or more substances subcutaneously into the bird. The substances injected using the injection apparatus as described herein may include, e.g., vaccines, medications or other therapeutic substances, vitamins, etc.

Referring to FIGS. 1-4, one illustrative embodiment of an injection apparatus as described herein is schematically depicted. In one or more embodiments, the injection apparatus 10 may include an engagement system 20 and an injection unit 30, both of which are configured to fold or bunched skin on a bird and inject one or more substances into the bird.

In one or more embodiments, the engagement system 20 may include a first capture member 22 and a second capture member 24. The first and second capture members 22 and 24 may, in one or more embodiments, be positioned to define a capture gap 40 between the first capture member 22 and the second capture member 40. In one or more embodiments, the first capture member 22 may be configured to rotate about a first axis 21 in a capture direction, wherein skin of a bird contacting the first capture member 22 in the capture gap 40 is pushed or drawn towards the second capture member 24 by the first capture member 22 rotating in the capture direction. In one or more embodiments the capture direction may be described as being a direction which an outer surface of the first capture member 22 is moving towards the second capture member 24.

In one or more embodiments, the second capture member 24 may also be configured to rotate in a capture direction about a second axis 23. In one or more embodiments, the first axis 21 is aligned with the second axis 23. In one or more alternative embodiments, the first axis 21 may be parallel to the second axis 23. In embodiments in which the first capture member 22 rotates in a clockwise capture direction about the first axis 21, the second capture member 24 rotates in a counterclockwise capture direction about the second axis 23 to draw the skin of a bird into the capture gap 40. In one or more other embodiments, the first capture member 22 may be described as rotating in a counterclockwise capture direction about the first axis 21 while the second capture member 24 rotates in a clockwise direction about the second axis 23 to draw the skin of a the bird into the capture gap 40.

Rotation of the first and/or second capture members 22 and 24 may be accomplished using any suitable actuator mechanisms. Examples of some potentially suitable actuator mechanisms may include one or more of the following components, e.g., motors (e.g., stepper motors, DC motors, AC motors, air motors, hydraulic motors, etc.), a rack and pinion, belt drives, gear assemblies, etc.

In another manner of characterizing rotation of the first and second capture members of injection apparatus as described herein, the first and second capture members may be described as having counter rotational movement such that the capture direction of each of the capture members may be described as being a direction which the outer surfaces of the capture members move towards each other in the capture gap formed by the first and second capture members.

Although the illustrative embodiment of injection apparatus 10 includes first and second capture members 22 and 24, both of which rotate about their respective axes, in one or more embodiments only one of the capture members 22 or 24 may rotate about an axis while the other capture member defining the capture gap 40 does not rotate. In still other potential alternative embodiments, the speed at which the capture members rotate may be the same or different.

In one or more embodiments, one or both of the first and second capture members 22 and 24 may be in the form of generally cylindrical rollers, although the first and second capture members may have a variety of other shapes e.g. conical rollers, polygonal shapes (e.g., hexagonal, octagonal, etc.). Furthermore, the outer surfaces of one or both of the capture members may be selected to facilitate bunching of the skin of a bird positioned in the capture gap 40. For example, the outer surfaces of one or both of the capture members may be constructed of one or more materials that have a relatively high coefficient of friction with respect to the skin and/or feathers of a bird such as, e.g., silicones, neoprene, urethanes, etc.

The injection apparatus 10 as described herein also includes an injection unit 30 operably coupled to the engagement system 20. In one or more embodiments, the injection unit 30 includes an injection needle 32 and a needle actuator 34 operably connected to the injection needle 34. The needle actuator 34 is, in one or more embodiments, configured to move the injection needle 32 between an injection position and a retracted position. In one or more embodiments, the injection needle 32 moves towards the first and second capture members 22 and 24 when moving from the retracted position to the injection position.

Figure 3:
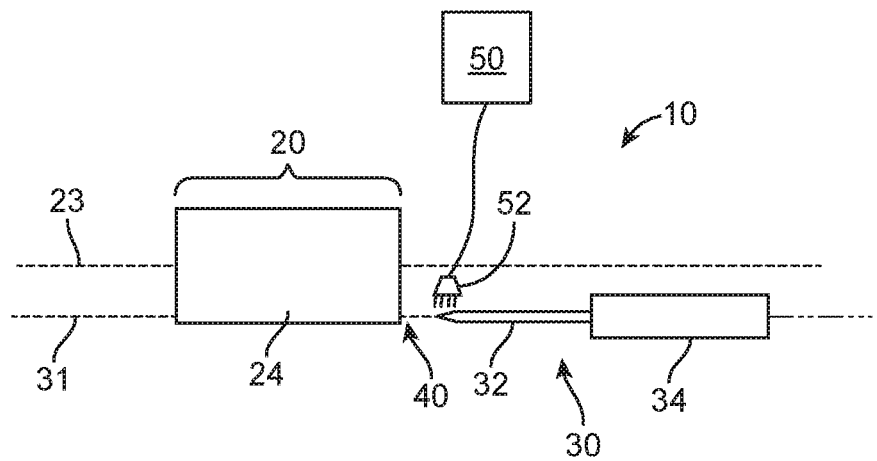
FIG. 3 is a side view of the injection apparatus of FIG. 1.
Figure 4:
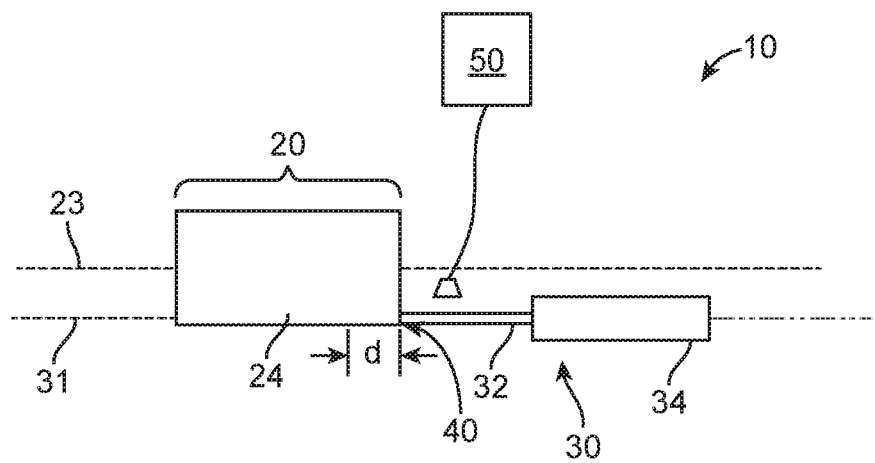
FIG. 4 is a view of the injection apparatus of FIG. 3, wherein the injection unit is advanced from the retracted position to the injection position.

In the illustrative embodiment depicted in, e.g., FIGS. 3 and 4, the injection needle 32 is in a retracted position in FIG. 3 and an injection position in FIG. 4. In one or more embodiments, the injection needle 32 may be described as including a tip portion at its distal end, with the tip portion being located in the capture gap 40 between the first and second capture members 22 and 24 when the injection needle 32 is in the injection position as depicted in FIG. 4. In one or more embodiments, the injection needle 32 includes a hollow passageway terminating in one or more openings in the tip portion of the injection needle 32 such that substances to be injected into a bird may pass through the hollow passageway in the injection needle 32 and enter a bird through the opening in the injection needle 32.

In one or more embodiments, the injection unit 30 may be configured to move the injection needle 32 between the injection position and the retracted position along an injection axis 31. In one or more embodiments, the injection axis 31 may be aligned with the first axis 21 and/or the second axis 23. In one or more alternative embodiments, the injection axis 31 may be parallel to the first axis 21 and/or the second axis 23.

As discussed herein, the injection unit 30 is configured to move the injection needle 32 between an injection position and a retracted position. When located in the injection position, the tip portion of the injection needle 32 is located in the capture gap formed between the first and second capture members as described herein. When a bird is positioned such that its skin is bunched or folded in the capture gap, movement of the injection needle 32 into the injection position will typically result in penetration of the skin of the bird by injection needle 32, allowing for delivery of one or more substances into the bird as described herein. When the injection needle 32 is in the retracted position, the injection needle 32 is not located in the capture gap 40 and is not, therefore, interfere with positioning of any portion of a bird in the capture gap. Furthermore, movement of the injection needle 32 from the injection position to the retracted position after delivering one or more substances into a bird, results in removal of the injection needle 32 from the bird.

In one or more embodiments, the actuator 34 configured to move the injection needle 32 from the retracted position to the injection position may move the injection needle 32 a selected distance into the capture gap. In one or more embodiments, the injection needle 32 may be described as occupying an injection depth d (see, e.g., FIG. 4) measured from a front edge of the capture members 22 and 24 in the capture gap 40 between the first and second capture members 22 and 24. The injection depth may be selected based on a variety of factors such as, e.g., the size of the first and second capture members, the size of the needle, the size and/or species of bird being injected, etc.

In one or more embodiments, the injection depth may, at a lower end, be, e.g., 5 millimeters or more, 10 millimeters or more, or 15 millimeters or more. In one or more embodiments, the injection depth may, at an upper end, be, e.g., 10 millimeters or less, 15 millimeters or less, 20 millimeters or less, or 25 millimeters or less. In one or more embodiments, the injection depth may be controlled to fall within a range of 12 millimeters to 15 millimeters.

In one or more embodiments, the injection depth d may define the distance over which the injection needle of an injection apparatus as described herein moves when moving between its retracted and injection positions. For example, the injection needle of one or more embodiments of an injection apparatus as described herein may move 5 millimeters or more, 10 millimeters or more, or 15 millimeters or more when moving between its retracted and injection positions. At an upper end, the injection needle of one or more embodiments of an injection apparatus as described herein may move, e.g., 10 millimeters or less, 15 millimeters or less, 20 millimeters or less, or 25 millimeters or less when moving between its retracted and injection positions. In one or more embodiments, the injection needle may move within a range of 12 millimeters to 15 millimeters when moving between its retracted and injection positions.

In one or more embodiments, the injection unit 30 may include a fluid supply 36 configured to deliver fluids to the injection needle 32 for injection into a bird located in the capture gap 40. The fluid supply 36 may include one or more reservoirs, one or more pumps, one or more valves, etc. needed to deliver the substance or substances to be injected into a bird through the injection needle 32.

In one or more embodiments of the injection apparatus as described herein, the injection apparatus 10 may include a sanitizing apparatus 50 (see, e.g., FIGS. 3 and 4) that is configured to sanitize the injection needle 32 at one or more selected times. As used herein, the term "sanitize" means treatment of the injection needle such that the transfer of infectious agents or other Biologics between birds treated using the injection apparatus described herein may be substantially reduced. The sanitizing apparatus 50 may, in one or more embodiments, be configured to sanitize the injection needle when the injection needle 32 is in a retracted position. In still one or more other embodiments, the sanitizing apparatus 50 may be configured to sanitize the injection needle 32 as it moves between the injection position and the retracted position.

In one or more embodiments, the sanitizing apparatus 50 may include one or more reservoirs, one or more pumps, and one or more valves configured to deliver a sanitizing liquid (such as e.g., isopropyl alcohol) that is sprayed or otherwise delivered to the injection needle 32. In one or more alternative embodiments, the sanitizing apparatus 50 may involve the use of e.g., UV light to perform and/or assist with the sanitizing process.

Figure 5:
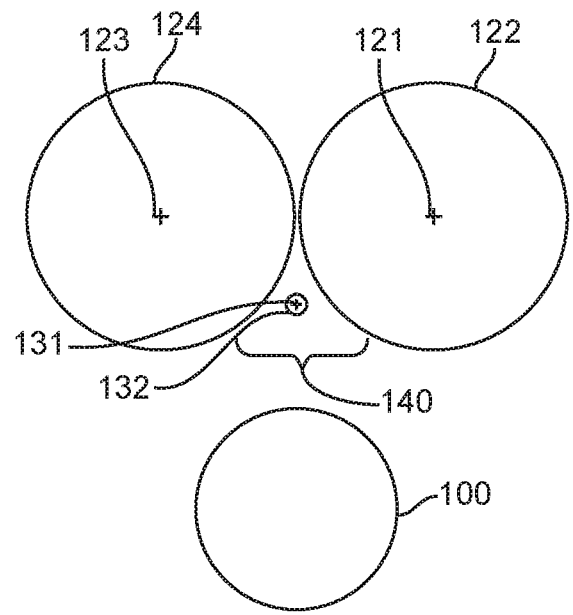
FIG. 5 is a schematic diagram of another illustrative embodiment of the injection apparatus as described herein depicting one embodiment of an arrangement of the engagement system relative to the injection needle and a portion of a bird.
Figure 6:
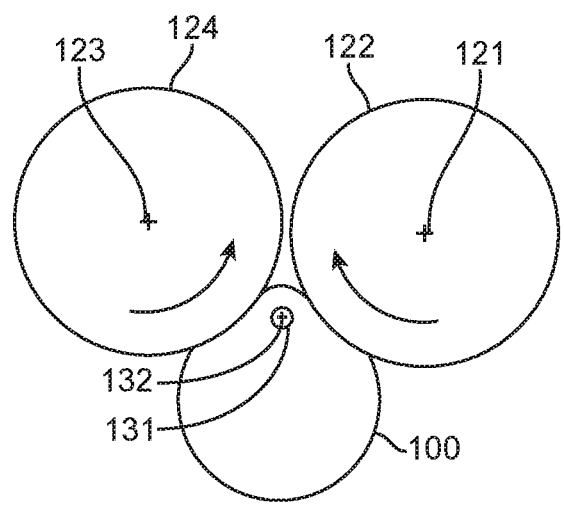
FIG. 6 is a view of the injection apparatus of FIG. 5 depicting one embodiment of an arrangement of the engagement system with the bird to facilitate injection of a substance into the bird.

Referring to FIGS. 5 and 6, another illustrative embodiment of an injection apparatus is schematically depicted to illustrate one embodiment of a method of using the injection apparatus as described herein. The depicted injection apparatus includes a first capture members 122 and a second capture member 124. The first capture member 122 is configured to rotate about a first axis 121 in the depicted direction, while the second capture member 124 is configured to rotate about a second axis 123 in the depicted direction. As discussed herein, the first and second capture members 122 and 124 rotate in opposite directions around their respective axes such that the outer surfaces of the capture members rotate towards each other in the capture gap 140 defined between the capture members 122 and 124. Also depicted in FIGS. 5 and 6 is an injection needle 132 which moves into and out of the capture gap 140 along an injection axis 131 as discussed above in connection with FIGS. 1-4.

To illustrate the method of using injection apparatus as described herein, an exemplary bird 100 is depicted in FIGS. 5 and 6 in the form of a circle, although be understood that the shape of a portion of a bird into which the injection needle moves will not typically be in the form of a circle. For the purposes of illustration however, a circle will be used to represent the portion of the bird drawn into the capture gap 140 using the capture members as described herein.

As depicted in FIG. 5, the bird 100 is positioned outside of the capture gap 140 at the start of the process. Furthermore, it will also be understood that the injection needle 132 is not located in the capture gap when the bird 100 is also not located in the capture gap. As a result, movement of the bird into the capture gap 140 is possible without interference from the injection needle 132. In one or more embodiments, positioning of the bird 100 in the capture gap 140 between the capture members 122 and 124 may be accomplished by moving the bird 100 into the capture gap 140, moving the capture gap 140 (i.e., moving the first and second capture members 122 and 124) towards the bird 100, or a combination thereof (i.e., moving both the capture gap 140 and the bird 100 towards each other).

Regardless of the motion or motions required to position the bird 100 in the capture gap 140, a portion of the bird 100 is positioned in the capture gap 140 such that rotation of the first and second capture members 122 and 124 about their respective axes as depicted by the arrows in FIG. 6 preferably draws the skin of the bird 100 into the capture gap through frictional contact between the first and second capture members 122 and 124 and the skin and/or feathers of the bird 100 as depicted schematically in FIG. 6.

In one or more embodiments, one or both of the first and second capture members 122 and 124 may be rotating before the bird 100 is positioned in the capture gap 140 (i.e., the first and/or second capture members 122 and 124 may be rotating as the bird 100 is moved into the capture gap 140). In one or more alternative embodiments, one or both of the first and second capture members 122 and 124 may be stationary as the bird 100 is moved into the capture gap 140, with rotation beginning only after the bird is at least partially located in the capture gap 140.

In one or more embodiments of the injection apparatus described herein, one or both of the capture members 122 and 124 may rotate for a selected period of time after the bird is at least partially located in the capture gap 140. For example, in one or more embodiments of the injection apparatus described herein, one or both of the capture members 122 and 124 may be rotated for a selected period of time after the capture members 122 and 124 and bird 100 are in selected positions relative to each other such that at least a portion of the bird 100 is located in the capture gap 140 defined between the capture members 122 and 124. In one or more embodiments, that selected period of time may be, e.g., 100 milliseconds or more, 200 milliseconds or more, 300 milliseconds or more, etc.

In one or more embodiments of the injection apparatus described herein, one or both of the capture members 122 and 124 may be rotated until a selected rotational force (e.g., torque) is exerted on one or both of the capture members by the skin of a bird positioned in the capture gap 140. For example, in one or more embodiments of the injection apparatus described herein, one or both of the capture members 122 and 124 may be rotated until a selected rotational force (e.g., torque) is exerted on one or both of the capture members by the skin of a bird positioned in the capture gap 140 after the capture members 122 and 124 and bird 100 are in selected positions relative to each other such that at least a portion of the bird 100 is located in the capture gap 140 defined between the capture members 122 and 124. In one or more embodiments, that selected force may be, e.g., 0.1 Newton meters or more, 0.15 Newton meters or more, 0.2 Newton meters or more, etc.

In one or more embodiments of the injection apparatus described herein, one or both of the capture members 122 and 124 may be rotated over a selected angular range after the bird is at least partially located in the capture gap 140. For example, in one or more embodiments of the injection apparatus described herein, one or both of the capture members 122 and 124 may be rotated over a selected angular range after the capture members 122 and 124 and bird 100 are in selected positions relative to each other such that at least a portion of the bird 100 is located in the capture gap 140 defined between the capture members 122 and 124. In one or more embodiments, that selected angular range may be, e.g., 60 degrees or more, 90 degrees or more, 120 degrees or more, etc.

As depicted in FIG. 6, rotation of one or both of the capture members draws the skin of the bird 100 into the capture gap 140 such that it is consistently positioned such that one or more substances can be delivered into the bird 100 using the injection needle 132. In particular, the injection needle 132 can be advanced along the injection axis 131 into the injection position in which the tip portion of the injection needle 132 pierces the skin of the bird 100 located in the capture gap 140.

After the injection process is completed, the injection needle 132 may be withdrawn to the retracted position (see, e.g., FIG. 3) along the injection axis 131 such that the injection needle 132 is removed from the skin of the bird 100. After the injection needle is removed from the skin of the bird 100, the bird 100 may be moved out of the capture gap 140. Movement of the bird 100 out of the capture gap 140 may involve moving the capture members 122 and 124 away from the bird 100, moving the bird 100 away from the capture members 122 and 124, or a combination thereof (i.e., moving both the first and second capture members 122 and 124 and the bird 100 away from each other).

In one or more embodiments, removal of the bird 100 from the capture gap 140 may be facilitated by either stopping rotation of one or both of the first and second capture members 122 and 124. In one or more alternative embodiments, removal of the bird 100 from the capture gap 140 may be facilitated by reversing rotation of one or both of the first and second capture members 122 and 124 such that one or both of the capture members rotates in a release direction that is opposite the capture direction rotation used to draw the skin of the bird into the capture gap. In one or more embodiments of the injection apparatus described herein, one or both of the capture members 122 and 124 may be rotated in the release direction over a selected angular range to release the skin of the bird after the injection needle is moved to its retracted position. In one or more embodiments, that selected angular range may be, e.g., 60 degrees or more, 90 degrees or more, 120 degrees or more, etc.

Rotation of the first and/or second capture members 122 and 124 in injection apparatus as described herein may be controlled in a variety of different manners. For example, in one or more embodiments, one or both of the capture members may be rotated for a selected period of time as a bird is in the process of being positioned in the capture gap defined by the capture members or after the bird is in a selected position relative to the capture members. In one or more alternative embodiments, the force applied to the skin of a bird positioned in the capture gap may be measured and used to control rotation of one or both of the capture members. For example, one or both of the capture members may be rotated in a capture direction until a selected force is exerted on the skin of a bird located in the capture gap. In in one or more further alternative embodiments, one or both of the capture members may be rotated in a capture direction over a selected angular range (which may include more than one rotation of one or both of the capture members).

Figure 7:
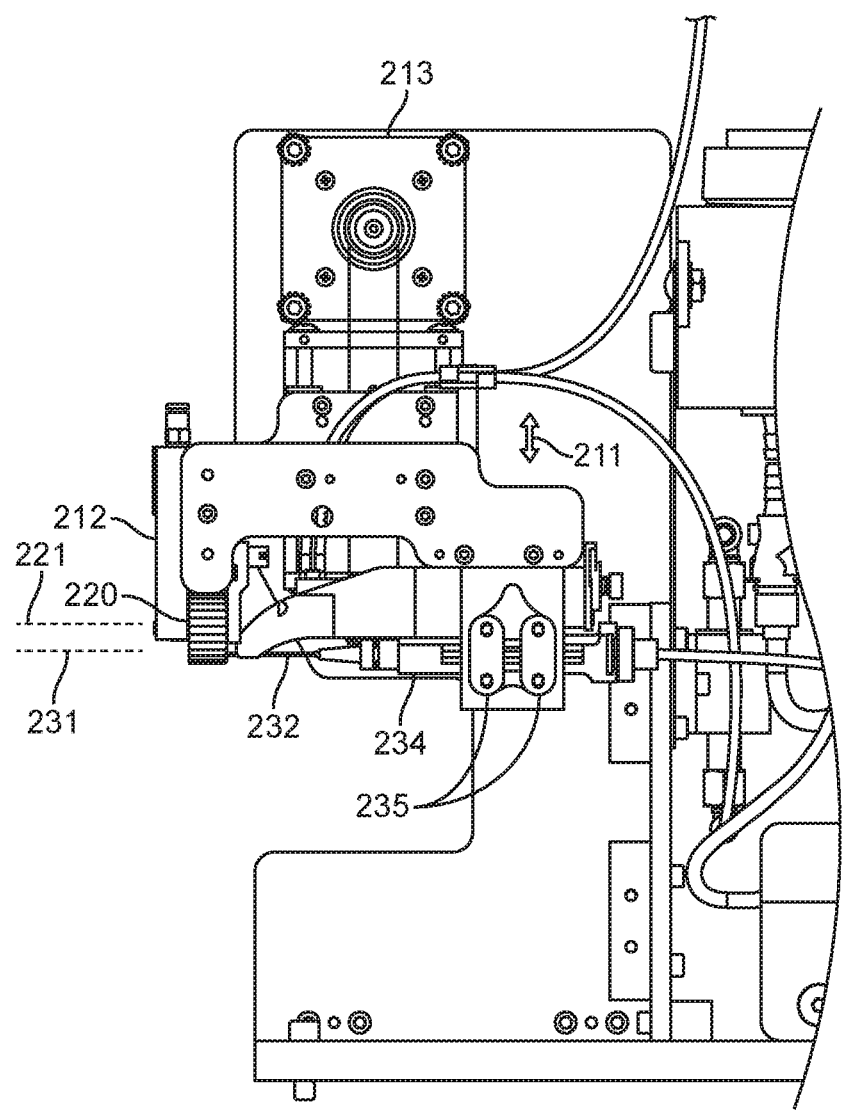
FIG. 7 depicts another illustrative embodiment of an injection apparatus as described herein.
Figure 8:
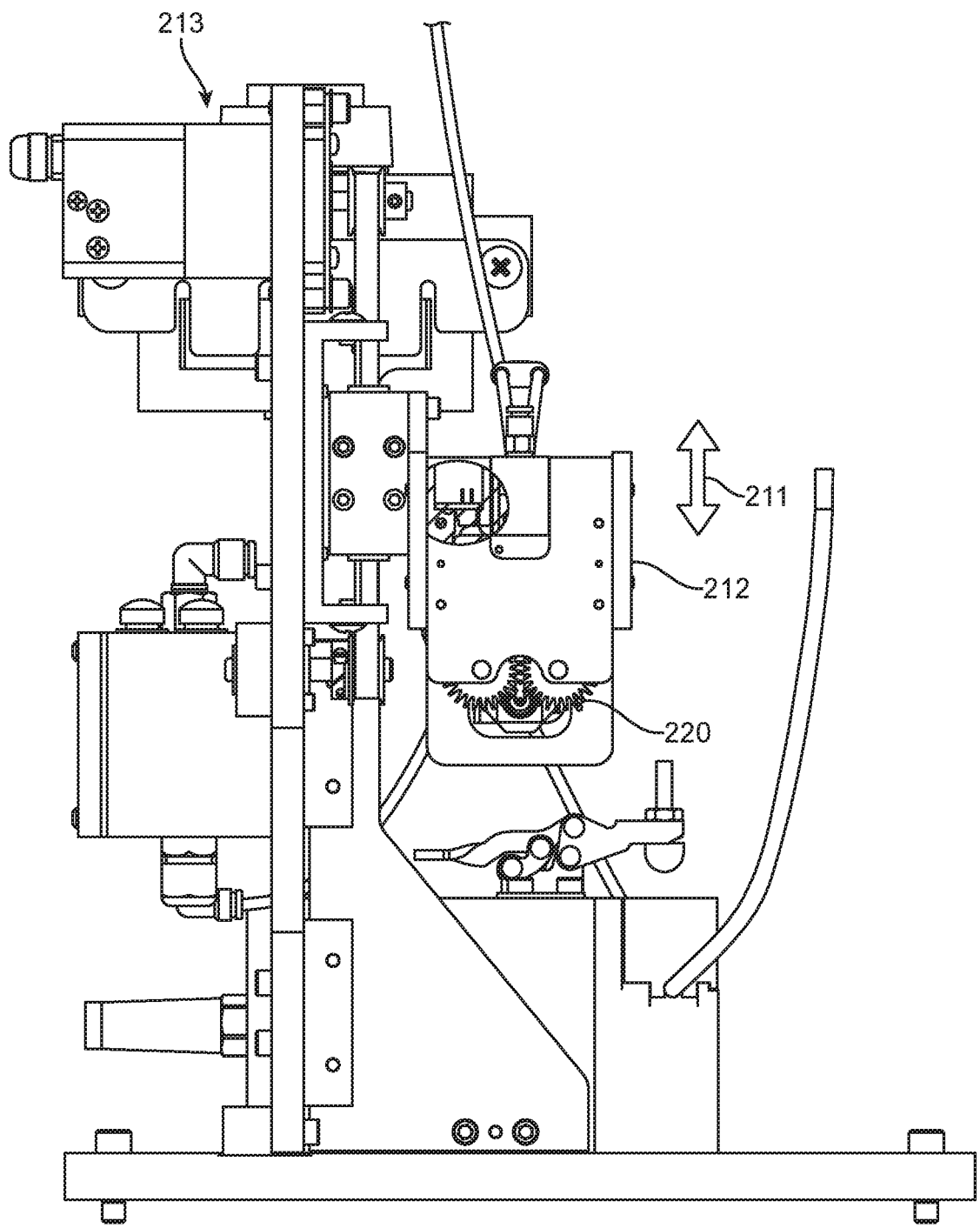
FIG. 8 depicts the injection apparatus of FIG. 7 as viewed from the left of the injection apparatus as depicted in FIG. 7.
Figure 9:
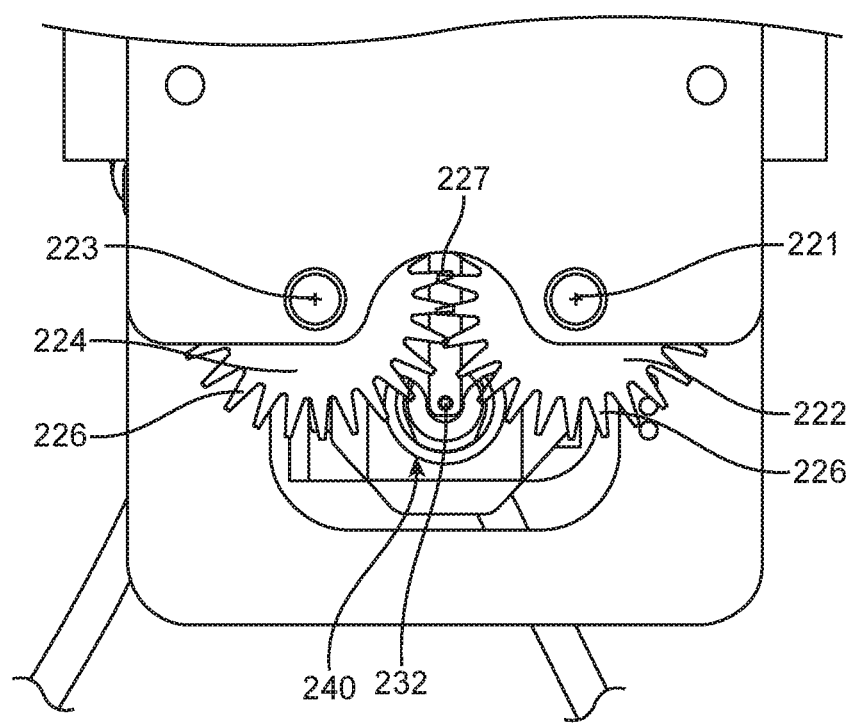
FIG. 9 is an enlarged view of a portion of the injection apparatus of FIGS. 7 and 8 as seen in FIG. 8.

Portions of another illustrative embodiment of an injection apparatus as described herein is depicted in FIGS. 7-9. In the illustrative embodiment seen in those figures, an engagement system 220 along with an injection needle 232 and injection needle actuator 234 are depicted as mounted on a carriage 212. As discussed in connection with other illustrative embodiments of the injection apparatus described herein, the engagement system 220 includes at least one capture member that rotates about an axis 221, while the injection needle 232 is movable between a retracted position and an injection position along an injection axis 231. In addition, the injection apparatus also includes injection needle position sensors 235 which may be used to monitor and/or control movement of the injection needle 232 between its retracted and injection positions.

In this illustrative embodiment of an injection apparatus as described herein, the engagement system 220 is configured for movement into directions as indicated by arrow 211 using a drive system 213 to move carriage 212 and the attached engagement system up and down. Movement of the carriage 212 is used to position the engagement system such that a bird is positioned in the capture gap defined in the engagement system 220. In this particular illustrative embodiment, a bird positioned beneath the engagement system 220 would be held stationary while the engagement system 220 is moved such that the bird is positioned in the capture gap defined by engagement system 220. Although the carriage 212 in the depicted embodiment is configured to move in translation, one or more alternative embodiments of injection apparatus as described herein may include a carriage configured to rotate such that the bird is positioned in the capture gap defined by engagement system. As discussed above, however, positioning a bird in the capture gap of engagement systems in injection apparatus as described herein, may involve movement of the bird while the engagement system is held stationary and/or movement of both the bird and the engagement system.

Positioning of the engagement system 220 relative to the bird may be accomplished by using a variety of different sensors and/or control systems. For example, in one or more embodiments, photocells, pressure sensors, proximity sensors, temperature sensors, etc. may be used to accurately position a bird in the capture gap of an engagement system. Furthermore, although the depicted drive system 213 includes a motor and belt drive, any suitable drive system, e.g., hydraulic pistons, solenoids, etc., could be used in place of a belt driven by a motor.

FIG. 9 is an enlarged view of a portion of the engagement system depicted in FIGS. 7 and 8. In particular, FIG. 9 depicts the capture members 222 and 224 along with their respective axes 221 and 223. Also depicted in this view is the injection needle 232 along with capture gap 240 defined by the capture members 222 and 224.

Another optional feature depicted in FIG. 9 are teeth 226 on each of the capture members 222 and 224. In one or more embodiments in which the capture members include teeth as depicted in, e.g., FIG. 9, the teeth 226 on the opposing capture members 222 and 224 may overlap each other as seen in the junction 227 between first and second capture members 224.

In one or more embodiments, the teeth 226 on the capture members may be constructed of resiliently flexible materials that may elastically deflect during contact with the skin of the bird in a capture gap and/or during rotation of the capture members where teeth 226 on opposing capture member contact each other. As discussed herein, elastic deflection of the teeth 226 may result in deformation of the teeth 226, however, that deformation is substantially recovered as the teeth 226 move out of contact with each other and/or the skin of a bird positioned in the capture gap 240. Illustrative examples of suitable materials that may be used to construct the teeth 226 may include, e.g., silicones, neoprene, urethanes, etc.

Another optional feature that may be found in one or more embodiments of the injection apparatus described herein that is depicted in connection with FIG. 9 is the spacing between the first and second capture members 222 and 224. In the embodiment depicted in that figure, capture members 222 and 224 overlap such that no gap exists between the capture members. In one or more alternative embodiments, however, a gap may be provided between the capture members where necessary for proper operation.

Figure 10:
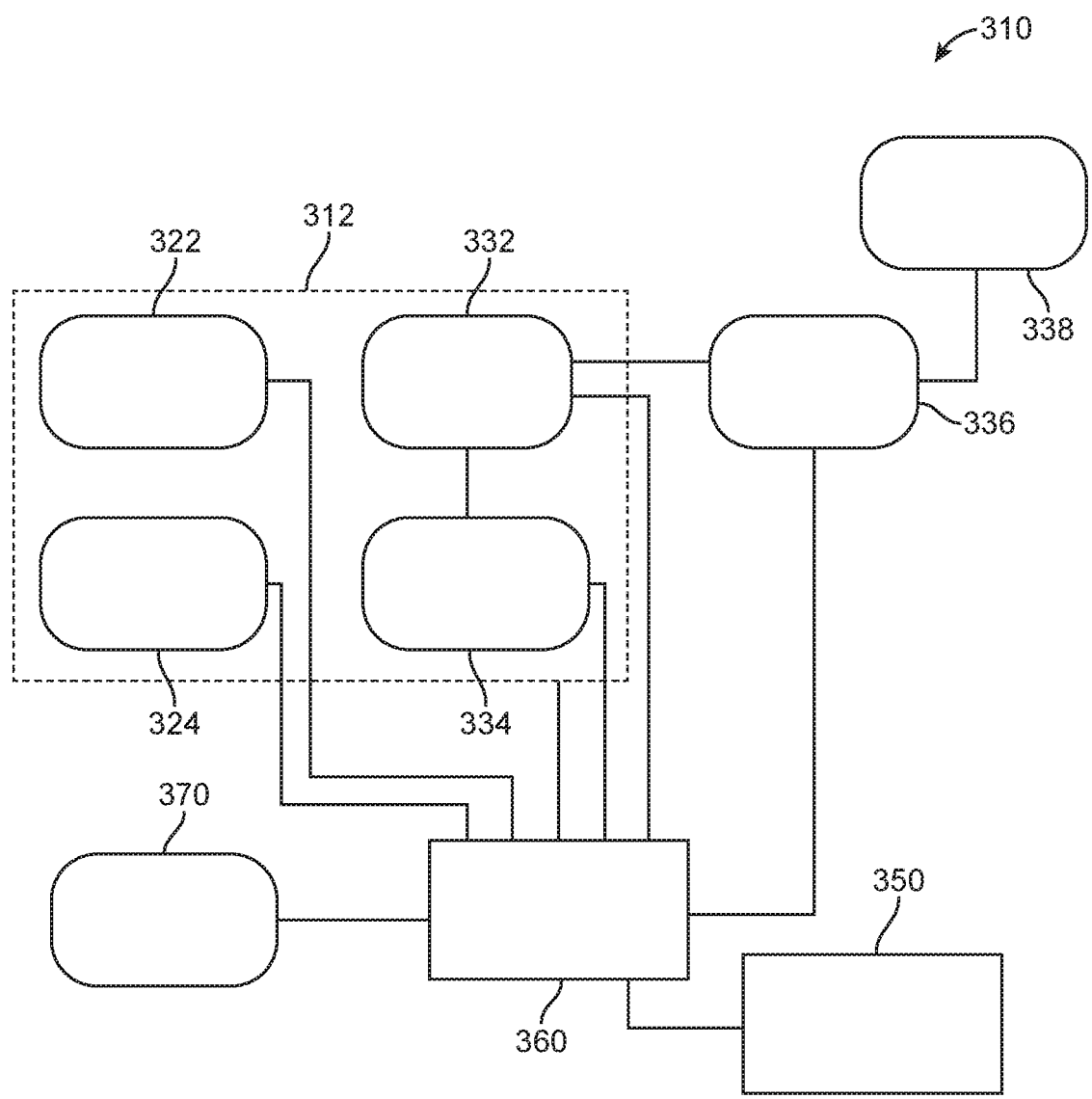
FIG. 10 is a schematic block diagram of various components that may be used in one or more embodiments of the injection apparatus as described herein.

FIG. 10 is a schematic block diagram of various components that may be used in one or more embodiments of the injection apparatus as described herein. The embodiment of injection apparatus 310 depicted in that figure includes a controller 360 that may be operably connected to various components in the injection apparatus 310. The controllers used in the injection apparatus described herein may be provided in any suitable form and may, for example, include memory and a control unit. In one or more embodiments, the control unit of a controller may, for example, be in the form of one or more microprocessors, Field-Programmable Gate Arrays (FPGA), Digital Signal Processors (DSP), microcontrollers, Application Specific Integrated Circuit (ASIC) state machines, etc.

Among the other components depicted in FIG. 10 are a carriage 312 on which a roller/capture member and its corresponding actuator 322, a second roller/capture member and its corresponding actuator 324. The actuators for both of the roller/capture member are, in the depicted embodiment, operably connected to the controller 360 to control their rotation as described herein. The controller 360 may be configured to control rotation of one or both of the capture members of injection apparatus as described herein based on, e.g., one or more of time, force (e.g., torque), angular rotation, etc.

An injection needle 332 and its corresponding injection unit actuator 334 are shown as located on the carriage 312. It should be understood, however, that all of these components may or may not be located on the carriage 312. For example, the injection needle 332 and its actuator 334 may or may not be located on the same carriage as the rollers and their corresponding actuators. In one or more embodiments, the actuator 334 of the injection unit may be operably connected to the controller 360.

Other components depicted in the injection apparatus 310 include a pump 336 and reservoir 338 which may be fluidly connected to the injection needle 332 to supply one or more substances to as described herein. The pump 336 may, in one or more embodiments, be operably connected to the controller 360 to control delivery of substances through the injection unit. Although not depicted on the carriage 312, the pump and/or reservoir may both be mounted on the carriage along with the rollers/capture members in one or more embodiments of the injection apparatus described herein.

Another component depicted in FIG. 10 as being operably connected to the controller 360 is a sanitizing apparatus 350 which may be used to sanitize the injection needle 332 as discussed herein.

Still another component depicted in FIG. 10 as being operably connected to the controller 360 is a bird indexer 370. The bird indexer 370 may be used to position a bird proximate to the capture gap formed between capture members of the engagement system as described herein. In one or more embodiments, the bird indexer 370 may move the bird towards the capture gap as well as positioned proximate the capture gap. In other embodiments, however, the bird indexer 370 may simply move the bird proximate the capture gap while the engagement system is moved relative to the bird to position the bird in the capture gap of the engagement system as described herein.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the poultry injection apparatus with rotating capture members and methods of using the same are discussed herein with some possible variations described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. An injection apparatus comprising:
an engagement system comprising:
a first capture member, and
a second capture member positioned to define a capture gap between the first capture member and the second capture member,
wherein the first capture member is configured to rotate about a first axis in a capture direction, wherein skin of a bird contacting the first capture member in the capture gap is pushed towards the second capture member by the first capture member rotating in the capture direction; and an injection unit operably coupled to the engagement system, wherein the injection unit comprises an injection needle and a needle actuator operably connected to the injection needle, wherein the needle actuator is configured to move the injection needle between an injection position and a retracted position, wherein the injection needle moves towards the first and second capture members when moving from the retracted position to the injection position, and wherein the injection needle moves between the injection position and the retracted position along an injection axis, wherein the injection axis is aligned with the first axis.

2. The injection apparatus of claim 1, wherein the injection needle comprises a tip portion, wherein the tip portion is located between the first and second capture member when the injection needle is in the injection position.

3. The injection apparatus of claim 1, wherein the first capture member comprises a first roller and teeth extending radially outward from the first roller, wherein the teeth of the first capture member rotate about the first axis when the first capture member rotates about the first axis.

4. The injection apparatus of claim 3, wherein the teeth of the first capture member are flexible such that the teeth of the first and second capture members elastically deflect when the first capture member is rotated past a location at which the teeth and the second capture member both contact the skin of the bird in the capture gap.

5. The injection apparatus of claim 3, wherein the second capture member comprises a second roller and teeth extending radially outward from the second roller, wherein the teeth of the first capture member mesh with the teeth of the second capture member.

6. The injection apparatus of claim 1, wherein the second capture member is configured to rotate about a second axis, wherein the first axis is aligned with the second axis, wherein the first capture member rotates in a clockwise direction about the first axis when rotating about the first axis in the capture direction and the second capture member rotates in a counterclockwise direction about the second axis to draw the skin of a the bird into the capture gap or the first capture member rotates in a counterclockwise direction about the first axis when rotating about the first axis in the capture direction and the second capture member rotates in a clockwise direction about the second axis to draw the skin of a the bird into the capture gap.

7. The injection apparatus of claim 6, wherein the first axis is parallel to the second axis.

8. The injection apparatus of claim 1, further comprising a sanitizing apparatus configured to sanitize the injection needle.

9. The injection apparatus of claim 8, wherein the sanitizing apparatus is configured to spray sanitizing liquid at the injection needle when the injection needle is in the retracted position.

10. The injection apparatus of claim 1, wherein the injection apparatus comprises a controller operably connected to the first capture member, wherein the controller is configured to rotate the first capture member in the capture direction about the first axis for a selected period of time after the bird is at least partially located in the capture gap.

11. The injection apparatus of claim 1, wherein the injection apparatus comprises a controller operably connected to the first capture member, wherein the controller is configured to rotate the first capture member in the capture direction about the first axis until a rotational force is exerted on one or both of the capture members by the skin of a bird positioned in the capture gap.

12. The injection apparatus of claim 1, wherein the injection apparatus comprises a controller operably connected to the first capture member, wherein the controller is configured to rotate the first capture member in the capture direction about the first axis over a selected angular range after the bird is at least partially located in the capture gap.

13. The injection apparatus of claim 1, wherein the injection needle moves five millimeters or more between the injection position and the retracted position.

14. The injection apparatus of claim 1, wherein the injection unit further comprises a needle position sensor configured to determine a location of the injection needle in the injection position.

15. A method comprising:
positioning skin of a bird in a capture gap between a first capture member and a second capture member;
rotating the first capture member in a capture direction about a first axis to push the skin of the bird in the capture gap towards the second capture member;
advancing an injection needle along an injection axis into an injection position after rotating the first capture member in the capture direction, wherein the injection axis is aligned with the first axis;
delivering selected material into the bird through the injection needle after advancing the injection needle into the injection position; and
retracting the injection needle to a retracted position from the injection position after delivering the selected material.

16. The method of claim 15, wherein first capture member rotates about the first axis in a release direction after retracting the injection needle to the retracted position, wherein the release direction rotation is opposite the capture direction rotation.

17. The method of claim 15, wherein the method further comprises rotating the second capture member in a second capture direction about a second axis when rotating the first capture member about the first axis, wherein the second capture member pushes the skin of the bird towards the first capture member when the second capture member rotates in the second capture direction.

18. The method of claim 17, wherein the second capture member rotates about the second axis in a release direction after retracting the injection needle to the retracted position, wherein the release direction rotation is opposite the capture direction rotation.

19. The method of claim 15, further comprising positioning the first and second capture member away from the skin of the live bird after releasing the skin of the live bird.

20. The method of claim 15, further comprising sanitizing the injection needle, after retracting the injection needle to the retracted position.

* * * * *